United States Patent [19]
Child

[11] 4,195,409
[45] Apr. 1, 1980

[54] DENTAL IMPLANT

[75] Inventor: Frank W. Child, Eagle Bend, Minn.

[73] Assignee: Child Laboratories Inc., Eagle Bend, Minn.

[21] Appl. No.: 877,073

[22] Filed: Feb. 13, 1978

[51] Int. Cl.² ............................................. A61C 13/00
[52] U.S. Cl. ..................................... 433/175; 433/201
[58] Field of Search ..................... 32/10 A; 128/92 E; 3/1

[56] References Cited

U.S. PATENT DOCUMENTS

| | | | |
|---|---|---|---|
| 2,210,424 | 8/1940 | Morrison | 32/10 A |
| 2,380,468 | 7/1945 | Saffir | 32/8 |
| 2,880,508 | 4/1959 | Lester et al. | 32/2 |
| 3,314,420 | 4/1967 | Smith et al. | 128/92 |
| 3,526,605 | 1/1970 | Bokros et al. | 3/1 |
| 3,605,123 | 9/1971 | Hahn | 3/1 |
| 3,707,006 | 12/1972 | Bokros et al. | 3/1 |
| 3,722,094 | 3/1973 | Rivoir | 32/2 |
| 3,863,344 | 2/1975 | Pillet | 32/10 A |
| 3,934,347 | 1/1976 | Lash | 32/10 A |
| 3,971,134 | 7/1976 | Bokros | 32/10 A |

*Primary Examiner*—Robert Peshock
*Attorney, Agent, or Firm*—Burd, Bartz & Gutenkauf

[57] ABSTRACT

A tooth prosthesis located in a mandible tooth socket having a root supporting a crown. The root has a cone-shaped head located in a recess in the bottom of the crown and a stem extended into the socket. An elastic body of ethylene vinyl acetate (EVA) copolymer surrounds and is bonded to the stem. The outer surface of the elastic body is bonded to the inside surface of a porous fabric which permits bone ingrowth to anchor the prosthesis to the mandible. The fabric has a pyrolite carbon outer skin. The upper edge of the fabric is spaced from the crown and head whereby the elastic body allows limited movement of the crown relative to the fabric.

36 Claims, 3 Drawing Figures

DENTAL IMPLANT

BACKGROUND OF INVENTION

Dental implants are used to replace lost natural teeth. The implants have root structures that are attached to the jaw bone. The root structures are made of metal and acrylic materials. These materials, being relatively rigid, do not have elasticity to minimize forces on the bone and provide the implant with yielding characteristics similar to a natural tooth.

Natural teeth have biomechanical toleration and dissipation of occlusional forces. The teeth have limited movement and return to their original positions after being subjected to a force, as chewing or mastication pressure.

Carbonaceous dental implants have been proposed to approximate the modulus of elasticity of natural bone to deal with the problems of stress concentration at the bone prothesis interface. Porous polymeric material has also been proposed to serve as an artificial periodontal ligament which allows attachment of the material to bone tissue through natural tissue growth.

SUMMARY OF INVENTION

The invention is directed to a prosthetic implant device attachable by natural ingrowth to the tissue of a primate or animal. More specifically, the invention is directed to a dental implant which can be inserted into a mandible tooth socket and attachable to the bone by natural bone ingrowth. The dental implant includes an apparatus for supporting a dental crown on a tooth-holding bone. The apparatus has a root having first and second portions. The first portion is adapted to be attached to the crown. In one embodiment, the first portion is a truncated cone-shaped head located in a correspondingly shaped recess in the bottom of the crown. An adhesive or suitable bonding material is used to permanently attach the crown to the head. The second portion of the root extends down into a socket in the bone. An elastic body surrounds and is mounted on the second portion. A porous means surrounds the elastic body and is secured thereto. The porous means and body have a shape for filling the tooth socket, whereby bone growth occurs into the porous means to anchor the root and body to the bone.

The elastic body has yielding characteristics so that the crown and root can simulate the movements of a natural tooth subjected to chewing pressure. In one form the elastic body can be an ethylene vinyl acetate (EVA) copolymer that is bonded to the inside surface of the fabric. The fabric can be a synthetic fiber coated with a pyrolitic carbon coating or skin. The inside surface of the fabric is bonded to the elastic body.

An annular portion of the elastic body separates the upper end of the fabric from the head of the root and the crown. This permits the root and crown to have limited movement in the axial and radial directions commensurate with the movement of a natural tooth.

An object of the invention is to provide a permanent dental implant that is anchored to the tooth-holding bone by natural bone ingrowth. A furthr object of the invention is to provide a dental implant which provides for limited movement of the crown and root of the implant in an axial and radial direction commensurate with the movement of a natural tooth. Another object of the invention is to provide a resilient mount for a root crown of a dental implant that functions to provide the crown and root with return movement back to its original position after a sideways displacement upon release of chewing pressure.

These and other objects of the invention are embodied in the following detailed description of one embodiment of the dental implant.

DETAILED DESCRIPTION OF ONE EMBODIMENT OF INVENTION

Figure 1:
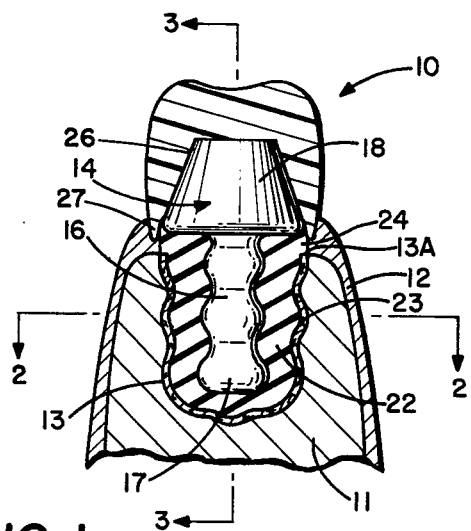
FIG. 1 is a transverse cross section of a jaw bone or human mandible provided with the dental implant of the invention.
Figure 2:
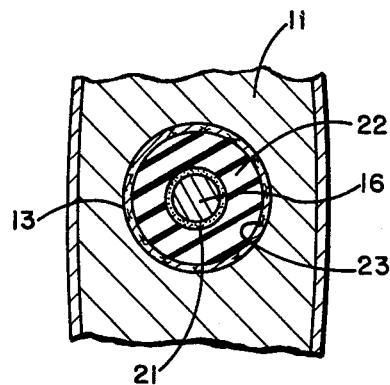
FIG. 2 is a sectional view taken along the line 2—2 of FIG. 1.
Figure 3:
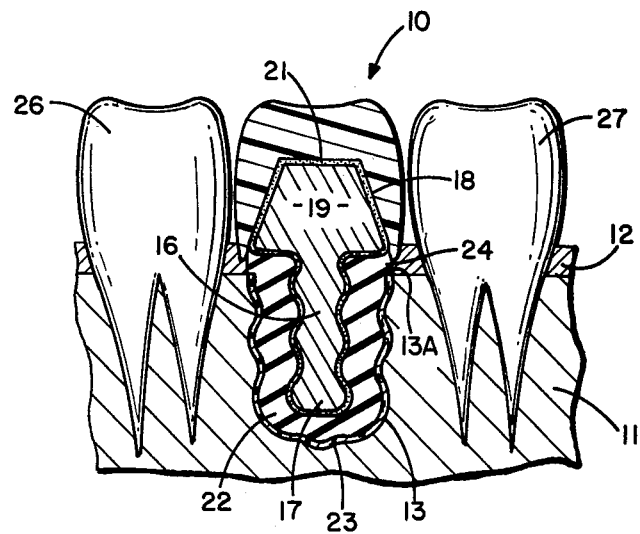
FIG. 3 is a sectional view taken along the line 3—3 of FIG. 1 showing the dental implant between two natural teeth.

Referring to FIGS. 1 and 3, there is shown a dental implant, indicated generally at 10, located in association with the jaw bone or mandible 11 of a primate. Natural tissue or gingiva 12 covers bone 11 and surrounds mid-portion of implant 10. Bone 11 has a prepared socket or cavity 13 accommodating a portion of implant 10. During the healing process natural tissue ingrowth of the bone anchors the implant to the bone. Socket 13 has a generally cylindrical shape. Other shapes of the socket can be used to accommodate and conform to the shape of the part of the dental implant located in the socket to minimize bone loss and firmly position the implant in the socket.

Implant 10 has a root indicated generally at 14 that serves as a base or skeleton for crown 25. Root 14 has a cylindrical body or stem 16 integrally joined to an enlarged generally cone-shaped head 18. The lower end of stem 16 has an enlarged base 17. Head 18 is a truncated cone-shaped member that is larger in diameter than the stem 16. Stem 16 extends downwardly from head 18 and has a corrugated or wave-like outer surface. Stem 16 can have other shapes, such as a smooth continuous cylindrical surface or a spiral or threaded outer surface.

Referring to FIG. 3, root 14 is a one-piece member having a base or substrate 19. Substrate 19 can be a carbon or graphite material, or a plastic material that is relatively rigid and has sufficient strength to withstand the biting and chewing. Substrate 19 is covered with an outer skin or layer 21. Preferably, layer 21 is a pyrolite carbon material positively joined to the outer surface of substrate 19. Pyrolite carbon skin 21 can have a plurality of carbon layers that are deposited on substrate 19 in a fluidized bed of hydrocarbon containing gaseous environment. The process of depositing pyrolite carbon in this manner is disclosed in U.S. Pat. No. 3,579,645 and U.S. Pat. No. 3,971,134.

Root 14 can be made of metal, as gold, titanium, Stellite-21, a ceramic, or a plastic material. The plastic materials include polypropylene, polycarbonate and CTEE fluorocarbons.

A sleeve or body 22 surrounds stem 16. Body 22 has an upper end bonded to the lower annular surface of head 18. The thickness of body 22 is uniform around stem 16. The outer surface of body 22 is corrugated and is complimentary to the corrugated surface of stem 16. Body 22 is an elastic member providing an elastic support for the root 14. Preferably, body 22 is an ethylene vinyl acetete (EVA) copolymer. In one example the EVA copolymer has a modulus of elasticity from $3.0 \times 10^6$ psi to $6.0 \times 10^6$ psi and a compressive strength in the direction along the axis of the root 14 of at least 200 lbs. and preferably at least 300 lbs. and a bending movement of at least 20 inch pounds and preferably at least 40 inch pounds.

Body 22 can be a plastic material, as Dow Corning Silastic, fluorosilicone rubber or a similar synthetic resinous plastic material. These materials are elastic and support root 14 for limited vertical and lateral movement. The elastic characteristic is less than the elastic characteristic of bone tissue. For example, body 22 may be about one quarter softer or more elastic than natural bone.

The outer surface of body 22 is covered with a porous cover or fabric 23. The inner surface of fabric 23 is bonded to the outer surface of body 22. The upper end of fabric 23 is spaced from the head 18 so that an annular portion 24 of the body 22 is between the lower edge of crown 25 and fabric 23. Fabric 23 fits into the socket 13 and bone 11. Fabric 23, being porous, allows attachment of the fabric to the bone tissue through the natural tissue growth of the bone. Fabric 23 can be a modified synthetic fiber, as Nylon or Teflon fibers or similar biologically inert material. The fabric 23 is coated with a pyrolite carbon coating or skin. The coated fabric 23 has a pore or space structure which permits a bone tissue attachment, while inhibiting calcification of the bone. The pore size is preferably between the range of 20 to 50 microns. The fabric 23 has a thickness of at least 0.1 mm. with only the inside surface of the fabric 23 bonded to body 22.

Fabric 23 is bonded to body 22 by placing body material in an uncured state and fabric 23 in a mold. The fabric surrounds the uncured body material. Pressure and heat is applied to the mold to melt or cure the body material, as EVA copolymer. An example of this process is disclosed in U.S. Pat. No. 3,579,645 and U.S. Pat. No. 3,971,134.

In use, as shown in FIG. 3, implant 10 is located between teeth 26 and 27, with stem 16 and body 22 positioned in socket 13 formed in bone 11. Fabric 23 is held in firm engagement with the walls of the socket 13 by the elastic body 22. Body 22 can be under slight compression as it is forced into socket 13. The upper end or edge 13A of fabric 13 is at approximately the bone level below tissue 12. Crown 25 has a truncated cone-shaped cavity 26 that accommodates head 18 of root 14. Suitable adhesives or cements are used to attach crown 25 to head 18. The lower edge 27 of crown 25 is in engagement with an annular portion of the upper end of elastic body 22. The lower edge 27 of crown 25 is also spaced from bone 11 and the upper end of fabric 13.

The elastic body 22 allows root 14 and crown 25 mounted thereon limited movement axially and radially commensurate with the movement of a natural tooth. Crown 25 will return to its original position after a sideways displacement as soon as the chewing pressure has been released from the crown. Elastic body 22 provides for an even distribution of the forces on the fabric 23, thereby applying a minimum of concentration of forces at any particular area of the fabric. This maintains interface between fabric 13 and the natural bone of the tooth socket. This fabric 23 will be attached to the bone tissue through the natural growth over a period of time. The dissipation of and dampening of the forces that are placed on crown 25 with elastic body 22 eliminates the abnormal stresses on the fabric 23 which would affect the tissue ingrowth into fabric 23. Fabric 23, being coated with pyrolite carbon, is compatible with the bone tissue and does not deteriorate in time. The carbon coating of the fabric also increases the strength of the fabric 23.

There has been shown and described a preferred embodiment of a dental implant. The changes in the materials, sizes, and dimensions of the parts of the dental implant can be made by those skilled in the art without departing from the invention. The invention is defined in the following claims.

The embodiments of the invention in which an exclusive property or privilege is claimed are defined as follows:

1. A prosthesis for tooth replacement in a living body comprising: a root having a head and a stem, a crown attached to the head, said crown having a cavity accommodating the head and an edge surrounding the cavity, an elastic body surrounding and mounted on the stem, said body having a portion located in engagement with said edge of the crown, and porous means surrounding the elastic body and secured thereto, said porous means and elastic-body being deformable for insertion into a mandible tooth socket whereby bone growth into the porous means anchors the root to the bone.

2. The prosthesis of claim 1 wherein: the head has a truncated cone shape and the crown has a truncated cone shape cavity for accommodating the cone shaped head.

3. The prosthesis of claim 1 wherein: the stem is a corrugated cylindrical member.

4. The prosthesis of claim 1 wherein: the outside surface of the elastic body has a corrugated shape.

5. The prosthesis of claim 1 including: at least one layer of pyrolite carbon covering the porous means.

6. The prosthesis of claim 1 wherein: the porous means is a fabric surrounding the body and bonded thereto, said fabric being spaced from the head and edge of the crown.

7. The prosthesis of claim 6 wherein: the elastic body engages the head and has a generally uniform thickness around the stem.

8. The prosthesis of claim 7 including: at least one layer of pyrolite carbon attached to the fabric.

9. The prosthesis of claim 6 wherein: the fabric has an inside surface and the body has an outside surface, said inside surface being bonded to the outside surface of the body.

10. The prosthesis of claim 1 wherein: the root has an outer layer of pyrolite carbon.

11. The prosthesis of claim 1 wherein: the porous means comprises a fabric bonded to the outside surface of the elastic body.

12. The prosthesis of claim 11 including: at least one layer of pyrolite carbon covering the fabric.

13. The prosthesis of claim 12 wherein: the fabric is spaced from the head and edge of the crown.

14. The prosthesis of claim 12 wherein: the elastic body has a uniform thickness around the stem.

15. The prosthesis of claim 1 wherein: the head has an annular surface surrounding the stem, said edge of the crown surrounding said annular surface and extended from the head in the direction of the stem.

16. The prosthesis of claim 15 wherein: said elastic body has an end bonded to said annular surface, said end having a portion located adjacent the edge of the crown.

17. An apparatus for tooth replacement in a living body comprising: crown means having an internal cavity, an edge surrounding the cavity, a root having an attached first portion and a second portion, said first portion located in the cavity and attached to the crown means, an elastic means mounted on the second portion, said elastic means having a portion located adjacent said edge of the crown means, and porous means surrounding the elastic means and secured thereto, said porous means and elastic means being deformable for insertion into a bone tooth socket whereby bone growth into the porous means anchors the root to the bone.

18. The apparatus of claim 17 including: at least one layer of pyrolite carbon covering the porous means.

19. The apparatus of claim 17 wherein: porous means is a fabric surrounding the elastic means and bonded thereto, said fabric being spaced from the first portion and crown means.

20. The apparatus of claim 19 wherein: the elastic means engages the first and second portions of the root and has a generally uniform thickness around the second portion of the root.

21. The apparatus of claim 20 including: at least one layer of pyrolite carbon attached to the fabric.

22. The apparatus of claim 19 wherein: the fabric has an inside surface and the elastic means has an outside surface, said inside surface being bonded to the outside surface of the elastic means.

23. The apparatus of claim 17 wherein: the root has an outer layer of pyrolite carbon.

24. The apparatus of claim 17 wherein: the porous means comprises a fabric bonded to the outside surface of the elastic means.

25. The apparatus of claim 24 including: at least one layer of pyrolite carbon covering the fabric.

26. The apparatus of claim 17 wherein: the elastic means has a generally uniform thickness around the second portion of the root.

27. An apparatus for supporting a member in a bone of a living body, said member having a cavity and an edge surrounding the cavity comprising: rigid means having an attached first portion and second portion, said first portion adapted to be located in the cavity and attached to the member, an elastic body mounted on the second portion, said body having a portion located in engagement with said edge of the member, and porous means surrounding the body and secured thereto, said porous means and body being deformable for insertion into a cavity in the bone whereby bone growth into the porous means anchors the rigid means to the bone.

28. The apparatus of claim 27 including: at least one layer of pyrolite carbon covering the porous means.

29. The apparatus of claim 27 wherein: porous means is a fabric surrounding the body and bonded thereto, said fabric being separated from the first portion.

30. The apparatus of claim 29 wherein: the elastic body engages the first and second portions of the rigid means and has a generally uniform thickness around the second portion of the rigid means.

31. The apparatus of claim 30 including: at least one layer of pyrolite carbon attached to the fabric.

32. The apparatus of claim 29 wherein: the fabric has an inside surface and the body has an outside surface, said inside surface being bonded to the outside surface of the body.

33. The apparatus of claim 27 wherein: the rigid means has an outer layer of pyrolite carbon.

34. The apparatus of claim 27 wherein: the porous means comprises a fabric bonded to the outside surface of the elastic body.

35. The apparatus of claim 27 including: at least one layer of pyrolite carbon covering the fabric.

36. The apparatus of claim 27 wherein: the body has a generally uniform thickness around the second portion of the rigid means.

* * * * *

UNITED STATES PATENT AND TRADEMARK OFFICE
CERTIFICATE OF CORRECTION

PATENT NO. : 4,195,409
DATED : April 1, 1980
INVENTOR(S) : Frank W. Child

It is certified that error appears in the above—identified patent and that said Letters Patent are hereby corrected as shown below:

Column 1, line 62, "furthr" should be --further--.

Column 3, line 30, "0.1" should be --.01--.

Signed and Sealed this

Fifteenth Day of July 1980

[SEAL]

Attest:

SIDNEY A. DIAMOND

Attesting Officer     Commissioner of Patents and Trademarks